US010859552B2

(12) United States Patent
Yao et al.

(10) Patent No.: US 10,859,552 B2
(45) Date of Patent: Dec. 8, 2020

(54) EDIBLE OIL ANALYSIS SYSTEM AND METHOD

(71) Applicant: The Hong Kong Polytechnic University, Hong Kong (CN)

(72) Inventors: Zhongping Yao, Hong Kong (CN); Cheuk Chi Albert Ng, Hong Kong (CN); Tsz-tsun Ng, Hong Kong (CN); Suying Li, Hong Kong (CN)

(73) Assignee: THE HONG KONG POLYTECHNIC UNIVERSITY, Kowloon (HK)

( * ) Notice: Subject to any disclaimer, the term of this patent is extended or adjusted under 35 U.S.C. 154(b) by 324 days.

(21) Appl. No.: 15/628,043

(22) Filed: Jun. 20, 2017

(65) Prior Publication Data

US 2018/0364210 A1    Dec. 20, 2018

(51) Int. Cl.
*G01N 33/03* (2006.01)
*H01J 49/16* (2006.01)
(Continued)

(52) U.S. Cl.
CPC ......... *G01N 33/03* (2013.01); *G01N 33/6851* (2013.01); *H01J 49/0009* (2013.01);
(Continued)

(58) Field of Classification Search
CPC .............. G01N 33/03; G01N 33/6851; G01N 33/6848; G01N 33/6842; G01N 2458/15;
(Continued)

(56) References Cited

U.S. PATENT DOCUMENTS

2002/0087273 A1*   7/2002   Anderson .............. G16B 50/00
                                                        702/19
2003/0119021 A1*   6/2003   Koster ................. C12Q 1/6834
                                                        435/6.12
(Continued)

FOREIGN PATENT DOCUMENTS

CN      102906851 A      1/2013
CN      103278591 A      9/2013
(Continued)

OTHER PUBLICATIONS

Yao., "Rapid authentication of edible oils by matrix-assisted laser desorption/ionization mass spectrometry", Database Compendex [Online] Engineering Information, Inc., May 14, 2017, XP002780308. (1 pages).
(Continued)

*Primary Examiner* — Lore R Jarrett
(74) *Attorney, Agent, or Firm* — Buchanan Ingersoll & Rooney PC

(57) ABSTRACT

The present disclosure provides a method and system for analysing one or more edible oil samples. In an embodiment the disclosure provides for calibrating the matrix-assisted laser desorption/ionisation mass spectrometry (MALDI-MS) data obtained for one or more edible oil samples to obtain calibrated spectral data; and comparing the calibrated spectral data derived from the one or more samples against a library of calibrated MALDI-MS spectra for a plurality of edible oil samples to determine the most likely composition of the one or more edible oil samples.

4 Claims, 22 Drawing Sheets

(51) Int. Cl.
*H01J 49/00* (2006.01)
*G01N 33/68* (2006.01)
*H01J 49/04* (2006.01)

(52) U.S. Cl.
CPC ........ *H01J 49/0036* (2013.01); *H01J 49/164* (2013.01); *H01J 49/0418* (2013.01)

(58) Field of Classification Search
CPC ........ G01N 2035/00158; H01J 49/0036; H01J 49/164; H01J 49/0009; H01J 49/0418; B82Y 30/00; G16B 30/00; G16B 50/00
See application file for complete search history.

(56) References Cited

U.S. PATENT DOCUMENTS

| | | | | |
|---|---|---|---|---|
| 2003/0138823 | A1* | 7/2003 | Brock | H01J 49/0418 435/6.11 |
| 2003/0214104 | A1* | 11/2003 | Chang | A63C 17/1418 280/11.204 |
| 2006/0293861 | A1* | 12/2006 | Askenazi | H01J 49/0036 702/22 |
| 2007/0087448 | A1* | 4/2007 | Nelsestuen | G01N 33/6848 436/173 |
| 2009/0221020 | A1* | 9/2009 | Smith | G01N 33/6851 435/29 |
| 2013/0054603 | A1* | 2/2013 | Birdwell | G06K 9/6224 707/738 |

FOREIGN PATENT DOCUMENTS

| | | |
|---|---|---|
| CN | 102590172 B | 1/2014 |
| CN | 105486744 A | 4/2016 |
| EP | 2580772 B1 | 3/2015 |
| TW | 201224428 A | 6/2012 |
| WO | 03/040715 A1 | 5/2003 |
| WO | 2010/141763 A1 | 12/2010 |
| WO | 2014/116872 A1 | 7/2014 |
| WO | 2016/141451 A1 | 9/2016 |

OTHER PUBLICATIONS

Extended European Search Report dated May 3, 2018, issued by the European Patent Office in corresponding European Application No. 17181140.9. (8 pages).
Ng et al., "Rapid screening of mixed edible oils and gutter oils by matrix-assisted laser desorption/ionization mass spectrometry", Anal. Chim. Acta, Jul. 16, 2015, vol. 884, pp. 70-76.
Lay et al., "Rapid characterization of edible oils by direct matrix-assisted laser desorption/ionization time-of-flight mass spectrometry analysis using triacylglycerols", Rapid Commun. Mass Spectrom, 2006, vol. 20, No. 6, pp. 952-958.
Picariello et al., "MALDI-TOF Mass Spectrometry Profiling of Polar and Nonpolar Fractions in Heated Vegetable Oils", Journal of Agricultural and Food Chemistry, May 22, 2009, vol. 57, No. 12, pp. 5391-5400.
Ng et al., "Supporting information—Rapid Screening of Mixed Edible Oils and Gutter Oils by Matrix-assisted Laser Desorption/Ionization Mass Spectrometry". (9 pages).
Zhang et al., "Authentication of edible vegetable oils adulterated with used frying oil by Fourier Transform Infrared Spectroscopy", Food Chemistry, 2012, vol. 132, pp. 1607-1613.
Jakab et al., "Differentiation of vegetable oils by mass spectrometry combined with statistical analysis", Rapid Communications in Mass Spectrometry, 2002, vol. 16, pp. 2291-2297.
International Search Report and Written Opinion of the International Searching Authority (Forms PCT/ISA/210 and PCT/ISA/237) dated Jan. 31, 2018, in corresponding international Application No. PCT/IB2017/053821. (8 pages).
Office Action dated Jul. 27, 2020, by the Chinese Patent Office in corresponding Chinese Patent Application No. 201710588321.1 and an English translation of the Office Action. (32 pages).

* cited by examiner

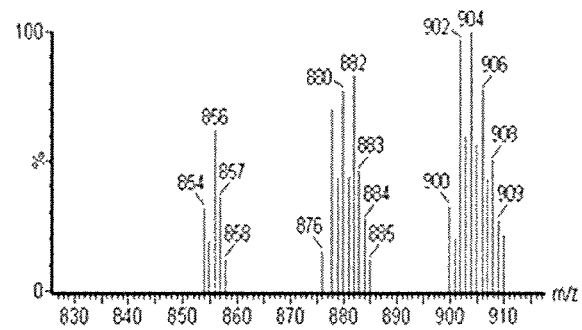
Fig 2a - Recycled oil sample 6
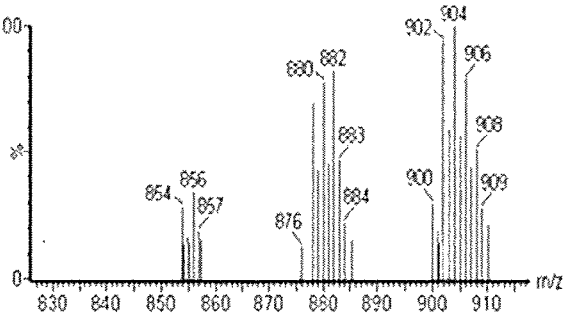
Fig 2b - Recycled oil sample 9
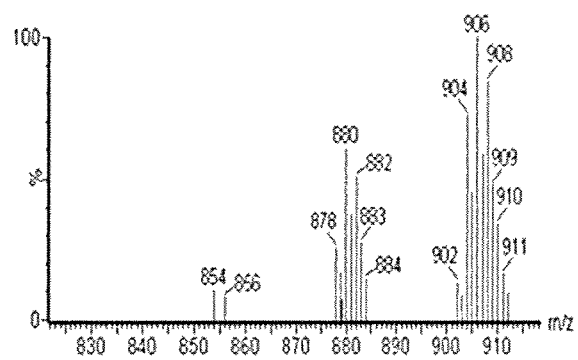
Fig 2c - Recycled oil sample 15
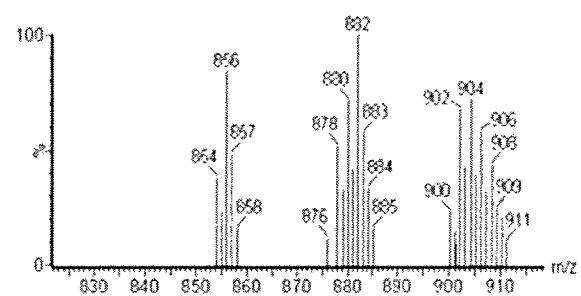
Fig 2d - Recycled oil sample 18
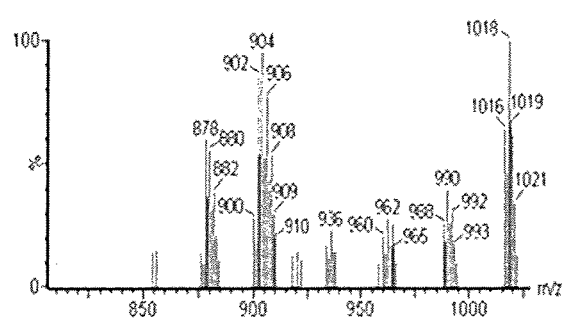
Fig 2e - Recycled oil sample 19
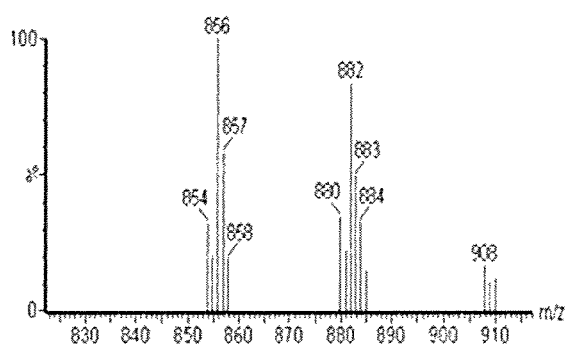
Fig 2f - Recycled oil sample 29

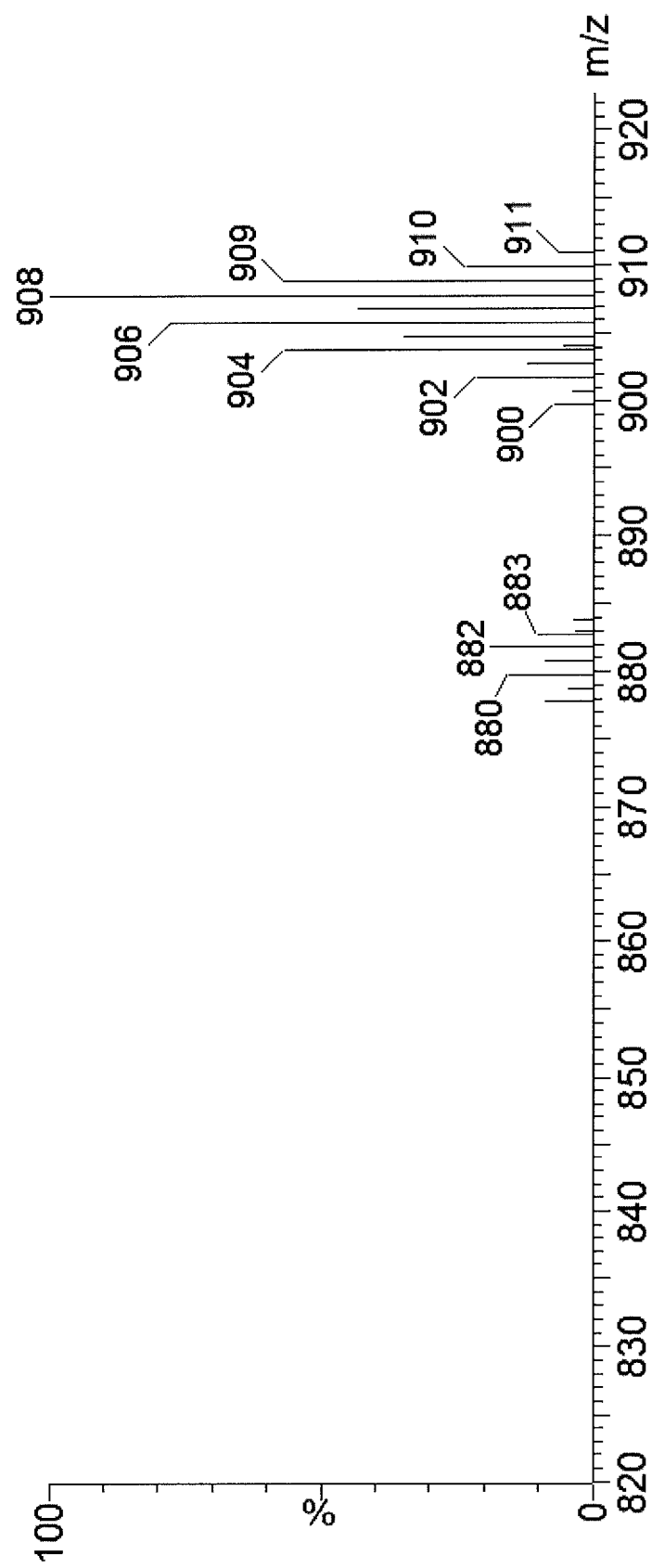
Fig 3a - 0% olive 100% canola

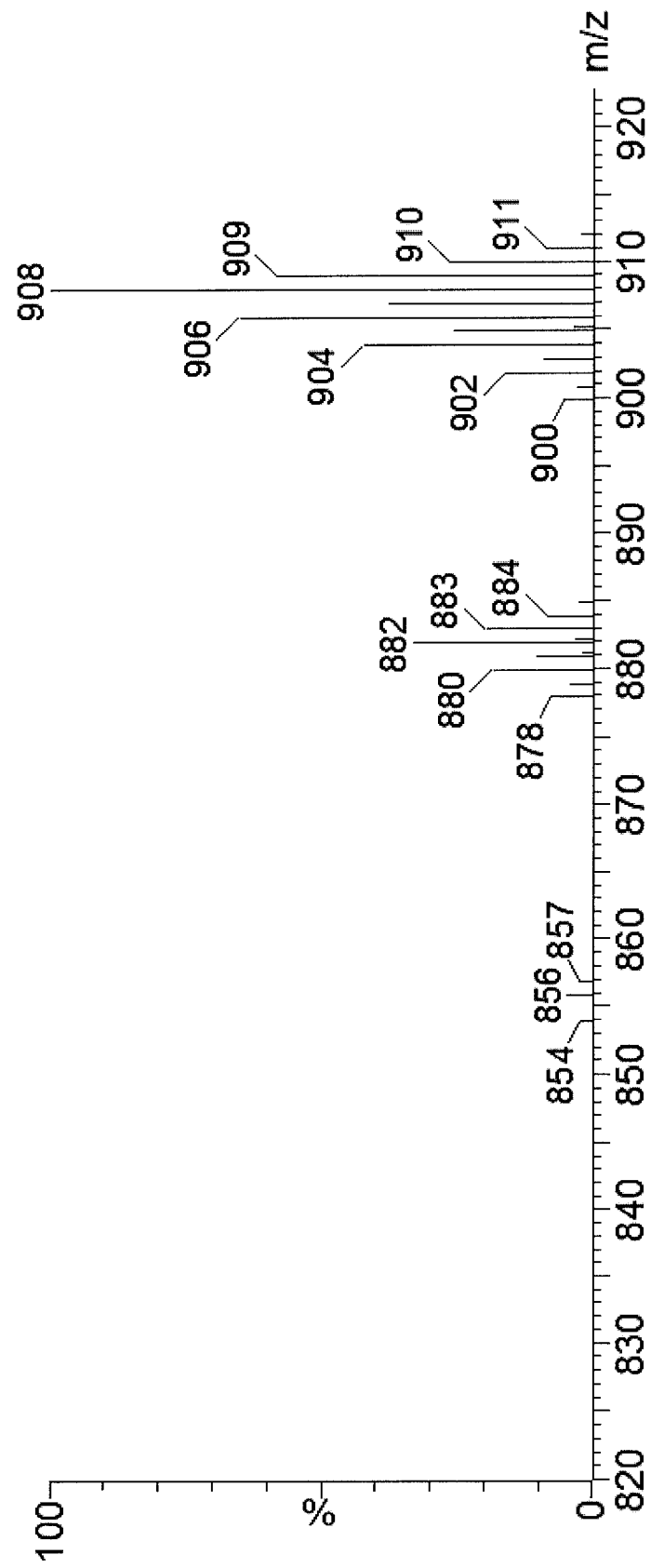
Fig 3b - 33% olive 67% canola

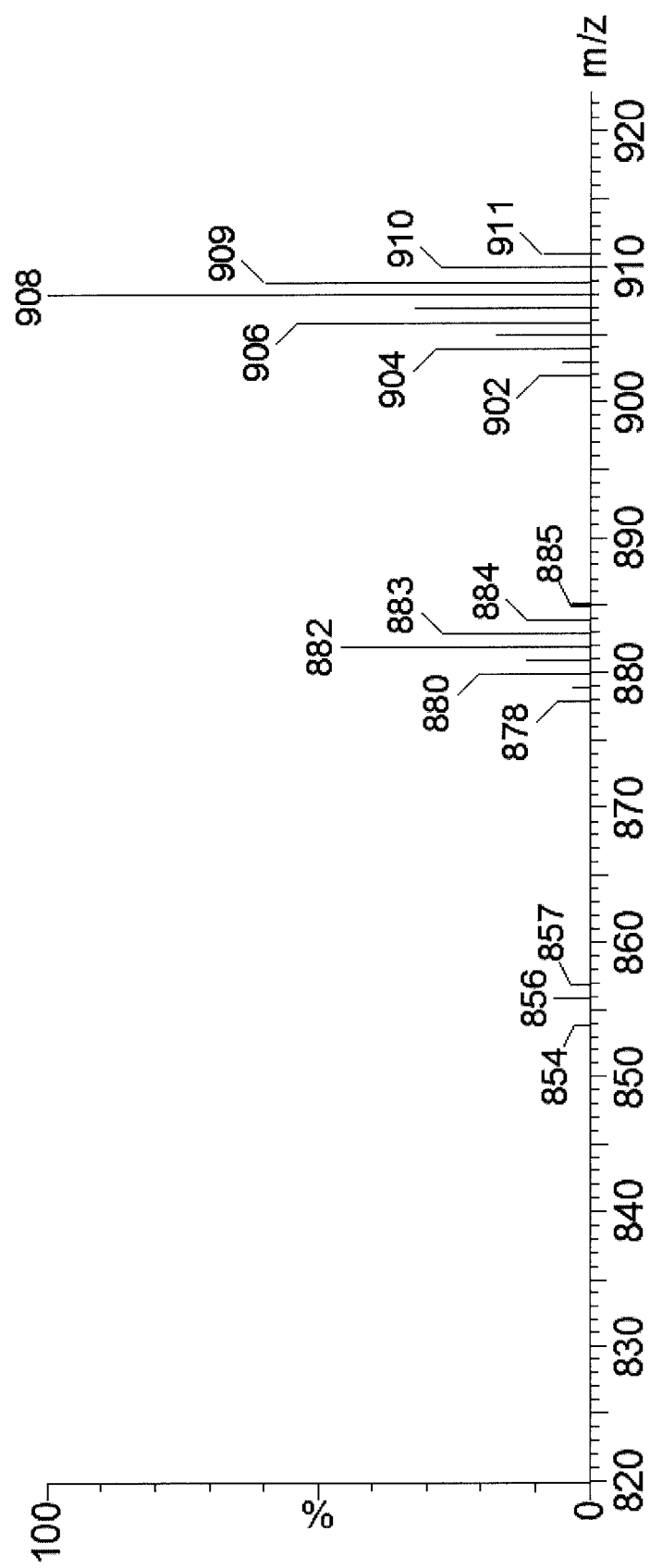
Fig 3c - 50% olive 50% canola

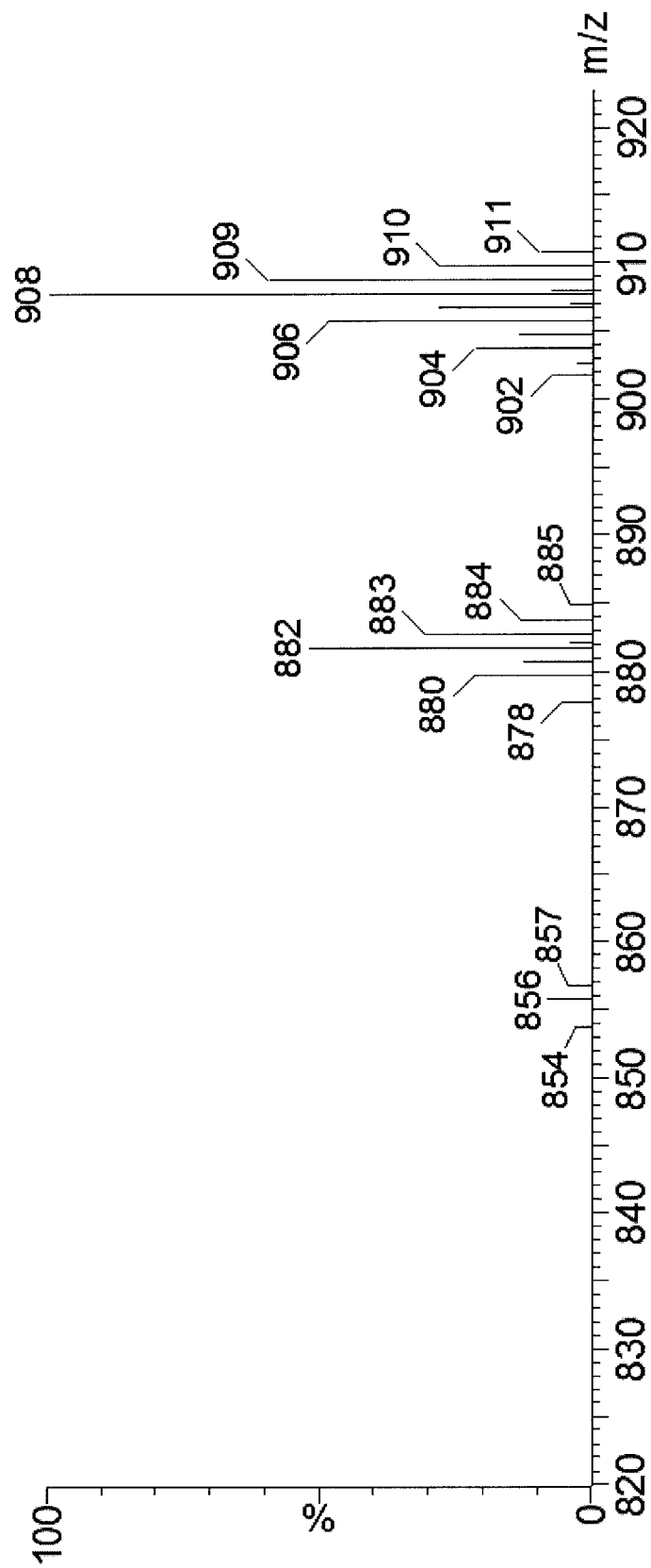
Fig 3d - 67% olive 33% canola

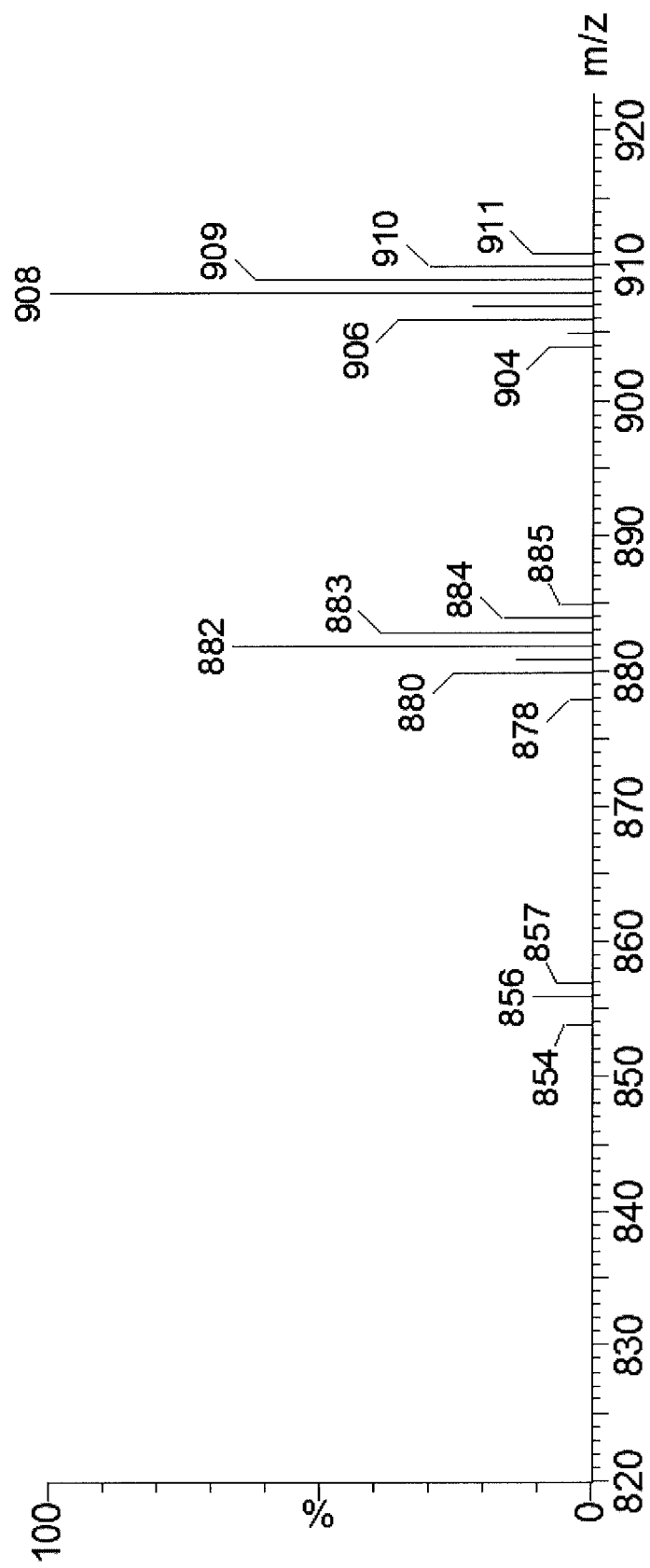
Fig 3e - 100% olive 0% canola

Home

Oil Authentication

Browse Oil Database
Almond oil
Avocado oil
Butter
Camellia oil
Canola (low erucic acid rapeseed) oil
Castor oil
Coconut oil
Corn oil
Cottonseed oil
Fish-Cod Liver oil
Fish-mixed-species oil

Oil Authentication

Please upload the raw MALDI-MS data file:

Drop the file here
-or-
Click to open the file Browser — 88

20170509-unknown-oil.txt
Status: Upload Complete

Match = Palm ; Correlation Score = 0.9959 —— 90

Fig 7a

Oil Authentication

Home

Oil Authentication

Browse Oil Database
Almond oil
Avocado oil
Butter
Camellia oil
Canola (low erucic acid rapeseed) oil
Castor oil
Coconut oil
Corn oil
Cottonseed oil
Fish-Cod Liver oil
Fish-mixed-species oil
Fish-unknown-species oil Please upload the raw MALDI-MS data file:

Drop the file here
-or-
Click to open the file Browser

20170411_s486_1_0_H6_1.txt
Status: Upload Complete

Match = PumpkinSeed ; Correlation Score = 0.9590 —— 92

20170411_s470_3_0_G12_1.txt
Status: Upload Complete

Match = Butter ; Correlation Score = 0.9410 —— 94

Fig 7b

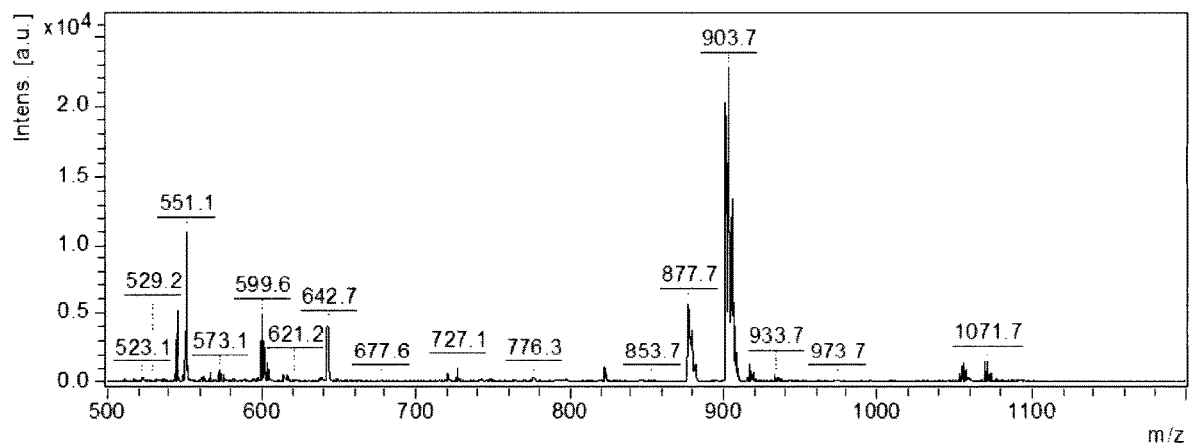
Problematic sample (claimed as flaxseed oil)
Fig 10a(i)
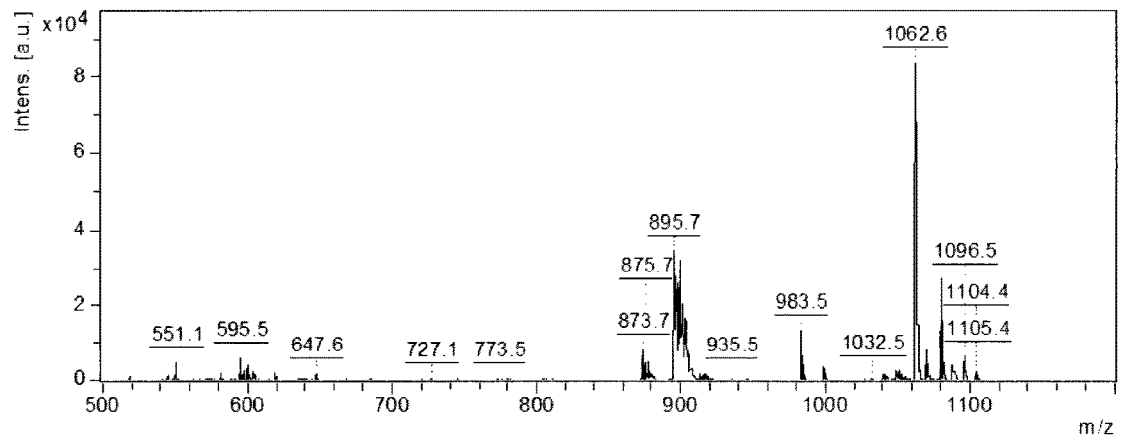
Typical flaxseed oil 1
Fig 10a(ii)

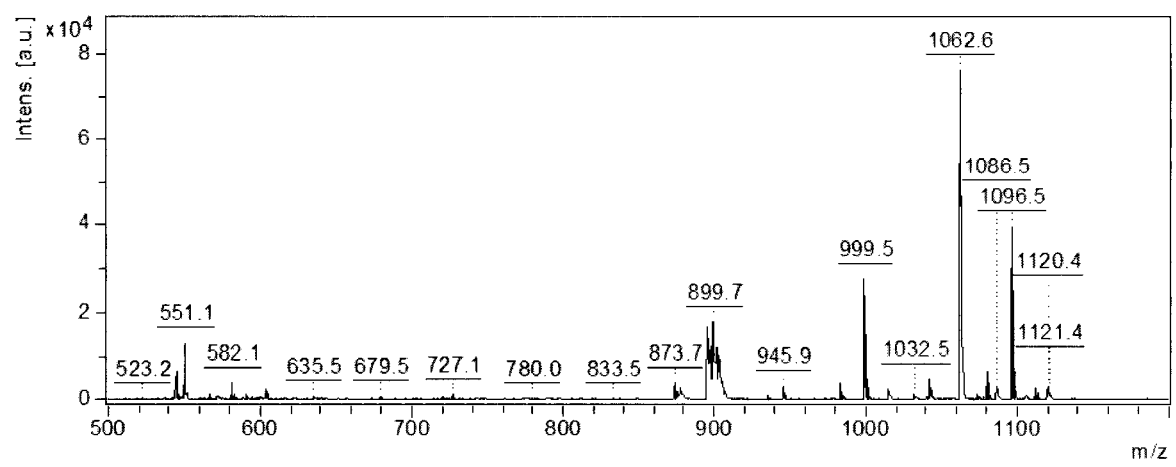
Typical flaxseed oil 2
Fig 10a(iii)

EDIBLE OIL ANALYSIS SYSTEM AND METHOD

FIELD OF THE INVENTION

The present invention relates to a system and method for identification of edible oils present in a sample using spectroscopic analysis, specifically matrix-assisted laser desorption/ionisation mass spectrometry (MALDI-MS), and matching sample data with spectral library of potential candidates.

BACKGROUND OF THE INVENTION

Increasing consumer health awareness and concern as to ingredients present in foods consumed has meant all entities in the food supply chain are needing to demonstrate the integrity and purity of ingredients used.

The integrity and purity of edible oils, particularly edible oils used for cooking, has attracted significant popular attention. In the Guangdong region of China (including Hong Kong) and also in Taiwan there have been many cases of adulterated oils ("gutter oils") where recycled oils have been used in place of quality edible oils.

One approach to determining authenticity of an edible oil sample is to focus on detecting food residue markers in the samples—markers which may include capsaicinoids (marker of chilli peppers), eugenol (marker of seasonings), undecanoic acid (marker of heated vegetable oils) and 13-methyl tetradecanoic acids (marker for animal oils). However, focussing on the presence or absence of these markers alone is not determinative of the authenticity of the edible oil sample; as unscrupulous suppliers may simply remove such markers.

Therefore, analysis using gas chromatography-flame ionisation detector (GC-FID) is the ISO-standard method to authenticate edible oils. In this method, the oil sample is first hydrolyzed using sodium hydroxide, and then converted to methyl esters of fatty acids using a boron trifluoride catalyst. The fatty acids methyl esters are then separated and detected using GC-FID.

The identities of the edible oil samples are then confirmed according to their fatty acids composition. Unfortunately, these procedures are relatively time-consuming and labour-intensive, meaning handling large amount of samples is not possible. Other methods such as liquid chromatography (LC)-based methods also have similar scalability problems.

In one effort to address the deficiencies of the above, a simple analytical protocol using matrix-assisted laser desorption/ionisation mass spectrometry (MALDI-MS) has been developed. (See e.g. Ng, T. T.; So, P. K.; Zheng, B.; Yao, Z. P., Rapid screening of mixed edible oils and gutter oils by matrix-assisted laser desorption/ionization mass spectrometry. Anal. Chim. Acta 2015, 884, 70-76.

MALDI-MS is widely used for the analysis of biological samples including lipids, and has simple sample preparation, short analysis time, and high sensitivity without chromatographic separation. The mass spectra of edible oils obtained from MALDI-MS are widely accepted as "fingerprints" for differentiation and authentication.

The spectrum produced by MALDI-MS is dominated by signals corresponding to diacylglycerols (DAGs)-like fragments and sodium adducts of triacylglycerols (TAGs). Lower mass region (100-500 Da) and higher mass region (1000-2000 Da) had also been investigated but typically no significant signals were obtained.

Heating and mixing of edible oils changes the composition of the edible oils, altering the TAG patterns of their MALDI-MS spectra. Prolonged heating of oils typically causes degradation of TAGs and formation of compounds such as diacylglycerols, monoacylglycerols, free fatty acids, oxidised TAGs and TAGs polymers. This change may be detected by comparison with reference spectra to determine identity and/or composition of a sample being tested.

In one approach to processing the MALDI-MS Spectrum to determine the authenticity/identity of a sample, principal component analysis (PCA) (a form of statistical analysis) is used to conduct a spectral comparison of the TAG peaks in the edible oil sample being analysed.

However, manually processing a MALDI-MS sample and using PCA analysis to identify a sample or verify the authenticity of a sample includes several non-trivial steps. The initial step of extraction of the relevant peaks requires manual selection by a trained operator, who has been trained to know which peaks to select.

The PCA analysis process itself can also be a source of error/complexity, because for some type of oils such as sunflower oil and grape-seed oil, their TAGs composition are similar to other oil species. This means several PCA steps are needed to differentiate the oils which can be very tedious.

Finally, the output of the PCA process is the projection of the input data onto the PCA plot, which compares the similarity between the sample and the data in the database. However, the identity of the sample cannot be displayed directly. From the PCA analysis, a trained operator is still required to draw a reasonable conclusion from the result.

TAGs patterns are considered to be the "fingerprint" of the edible oils. However, some of the species shared highly similar TAGs patterns (such as olive oil and avocado oil) which cannot be easily differentiated by PCA.

Previous approaches using PCA analysis have only considered TAG-relevant peaks in the PCA analysis. Other peaks, such as oxidation-related and cyclic peptide-related peaks, may also be useful. However, those additional peaks cannot be directly accommodated using the established PCA model, requiring remodelling of the PCA to fit the new information. Again, this process requires experienced and trained operators.

Unfortunately, therefore, when using PCA to analyse MALDI-MS spectra, the spectra still needs to be processed and matched manually by highly trained personnel, which is expensive, laborious and time-consuming and limits the capacity to scale MALDI-MS system for analysis of edible oils.

Accordingly, there exists a significant gap between where potential analysis of edible oils using MALDI-MS approaches needs to be and the current state at present.

It is an object of the present invention to provide a system and method which at least addresses or ameliorates some of the above problems or provides the public with an alternative choice.

SUMMARY OF THE INVENTION

Features and advantages of the disclosure will be set forth in the description which follows, and in part will be obvious from the description, or can be learned by practice of the herein disclosed principles. The features and advantages of the disclosure can be realised and obtained by means of the instruments and combinations particularly pointed out in the appended claims.

In accordance with a first aspect of the present invention, there is provided a method for analysing one or more edible oil samples, the method comprising:

calibrating the matrix-assisted laser desorption/ionisation mass spectrometry (MALDI-MS) data obtained for one or more edible oil samples to obtain calibrated spectral data; and comparing the calibrated spectral data derived from the one or more samples against a library of calibrated MALDI-MS spectra for a plurality of edible oil samples to determine the most likely composition of the one or more edible oil samples.

The comparison between calibrated MALDI-MS data derived from the one or more samples and a library of calibrated MALDI-MS spectra for a plurality of edible oil samples may be performed using a Cosine similarity test.

The most likely composition of the one or more edible oil samples may be determined after ranking, based on the calibrated MALDI-MS sample data, a plurality of library spectra of known edible oil types according to their likelihood of being in the sample, from most likely to least likely using cosine similarity test scores; and determining the most likely identification of the one or more edible oil samples based upon the highest ranked cosine similarity score.

Optionally, the cosine similarity test may conducted on one or more regions of the sample spectral data selected from the group comprising high mass, low mass and TAG regions and one or more corresponding regions of the edible oil samples in the library of calibrated MALDI-MS spectra.

Calibration may be performed by using at least one of TAG peaks and 2, 5-dihydroxybenzoic acid (DHB) matrix peaks as reference peaks.

Following calibration and before comparison with the calibrated library data, the sample data may be quantised by data binning. Data binning may be performed by dividing the entire spectra into intervals of 0.5 m/z, averaging the intensity of all readings within each bin, and setting the m/z reading as the m/z value at the middle of the interval.

Following binning, the sample data may be normalised by dividing the intensity of each bin with either the maximum intensity or the total intensity of all bins, multiplying by an appropriate scaling parameter and rounding to the nearest integer.

The comparison between calibrated MALDI-MS data derived from the one or more samples and a library of calibrated MALDI-MS spectra for a plurality of edible oil samples may also be performed using a statistical test selected from the group comprising characteristic peak matching methods, partial least squares discriminant analysis (PLS-DA), or decision tree-based methods.

In a further aspect of the present disclosure there is provided an edible oil sample identification system comprising:

an input system configured to receive matrix-assisted laser desorption/ionisation mass spectrometry (MALDI-MS) data for at least one or more edible oil samples;

a library comprising a plurality of calibrated MALDI-MS spectral data for a plurality of edible oil samples a processor configured to calibrate the MALDI-MS data derived from the one or more samples and compare it with the library to determine a predicted composition of the one or more edible oil samples.

The processor may be configured to compare the calibrated spectral data derived from the one or more samples with the library using a cosine similarity test, and to output the determined cosine similarity score for a plurality of samples of the library.

The processor may be configured to conduct the cosine similarity test on one or more regions of the sample spectral data selected from the group comprising high mass, low mass and TAG regions and one or more corresponding regions of the data in the library.

Calibration of the MALDI-MS Spectral data for the one or more samples and for the spectral data of the library may be performed by using at least one of TAG peaks and DHB matrix peaks as reference peaks.

Following calibration and before comparison against the calibrated library data, the processor may be configured to quantise the sample data by data binning.

In a further aspect of the present disclosure there is provided a method of generating a library of matrix-assisted laser desorption/ionisation mass spectrometry (MALDI-MS) data for a plurality of reference edible oil samples of a plurality of different types for identifying a sample other than the reference edible oil samples, the method comprising:

providing a plurality of reference samples of edible oil samples having a known type;

calibrating the MALDI-MS data for each of the plurality of reference edible oil samples by using at least one of TAG peaks and DHB matrix peaks as referential peaks;

quantising the MALDI-MS data for the edible oil samples by data binning;

normalizing the MALDI-MS data for the edible oil samples by dividing the intensity of each bin with either the intensity of the maximum bin or the total intensity of all bins; and associating the normalised MALDI-MS data with the edible oil type.

The present disclosure may also include computer program product, tangibly stored on machine readable storage device, the product comprising instructions operable to cause a processor to:

calibrate the matrix-assisted laser desorption/ionisation mass spectrometry (MALDI-MS) data obtained for one more edible oil samples; and compare the calibrated spectral data derived from the one or more samples against a library of calibrated MALDI-MS spectra for a plurality of edible oil samples to determine the most likely composition of the one or more edible oil samples.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings.

Preferred embodiments of the present invention will be explained in further detail below by way of examples and with reference to the accompanying drawings, in which:—

FIGS. 2a-2f show exemplary MALDI-MS spectra of various recycled oils.

FIGS. 3a-e depict exemplary MALDI-MS spectrum for mixture of canola and olive oils at various concentrations.

FIG. 6b shows an exemplary representation of an enlarged portion of the spectral region for the sample of FIG. 6a.

FIG. 7a depicts a strong correlation between an unknown sample of a pure oil and the reference sample for Palm oil stored in the library.

FIG. 7b depicts the results of an analysis of an unknown sample of an adulterated oil and the low correlation score with either Peanut or olive spectra in the reference sample.

FIG. 10a shows an exemplary sample mislabelled as Flaxseed oil.

DETAILED DESCRIPTION OF THE PREFERRED EMBODIMENTS

Figure 1A:
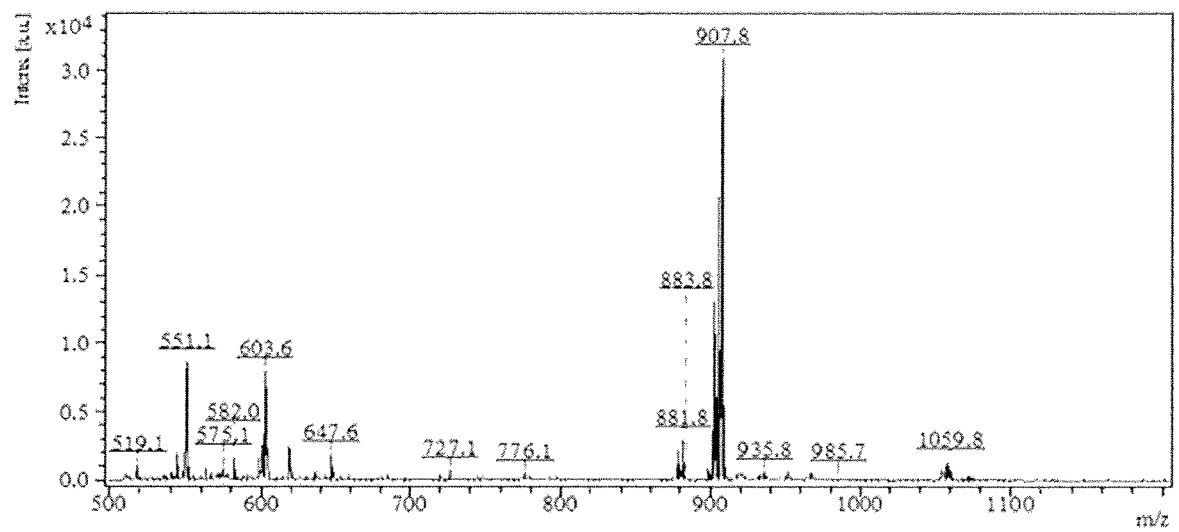
FIG. 1a depicts an exemplary MALDI mass spectrum for canola oil, showing the full spectrum from 500-1000 Da.

Various embodiments of the disclosure are discussed in detail below. While specific implementations are discussed, it should be understood that this is done for illustration purposes only. A person skilled in the relevant art will recognize that other components and configurations may be used without departing from the scope of the present disclosure.

The disclosed technology addresses the need in the art for a scalable, reliable technique for analysis of edible oils.
Typical MALDI Protocol for Analysis of Samples (Library and Unknown Samples)

Typical MALDI-MS protocol involved mixing of matrix solution and sample solution, which is subsequently allowed to dry onto the MALDI plate. After the formation of sample and matrix crystal, the MALDI plate is inserted into the MALDI-MS instrument for analysis.

No chromatographic separation is involved in MALDI-MS analysis, thus allowing rapid analysis of edible oil samples.

In the exemplary MALDI-MS protocol, edible oil samples could be loaded directly onto the MALDI plate pre-deposited with matrix layer for the MALDI-MS analysis. Sample loading for one sample could be finished within several seconds and around three hundred samples could be loaded onto the same MALDI plate.

In a specific steps of sample loading according to an exemplary approach used aliquots of 1 µL of 100 mg mL1 DHB in acetone were loaded onto spots of the MADLI plate and air-dried to form matrix layers. About 0.2 µL of each oil sample was then transferred by pipette tip or cotton tip to form a thin oil layer on the matrix layer.

The plate was then introduced into the mass spectrometer for MALDI-MS analysis.

An Ultraflex Xtreme MALDI-TOF/TOF mass spectrometer (Bruker Daltonics, Germany) was used for the analysis. The laser of the MALDI source was a Smart beam-II (Nd:YAG, 355 nm) pulse laser operating at a frequency of 2000 Hz. The mass spectrometer was operated in positive reflectron mode. The settings of positive reflectron mode for the ion source 1, source 2, lens, reflector 1, reflector 2, and pulsed ion extraction were 20.00 kV, 17.75 kV, 7.00 kV, 21.10 kV, 10.85 kV, and 140 ns, respectively. The sample rate and digitizer were set to 5.00 GS/s. Extended mass ranges were employed if necessary.

The mass spectrometer was calibrated with a PEG solution mixture (PEG600/PEG1000/PEG2000/NaI=1/2/2/5 (v/v)).

The spectral acquisition was performed using the flex-Control 3.4 (Bruker Daltonics, Germany) program. The mass spectra were analysed using flexAnalysis 3.4 (Bruker Daltonics, Germany) program. The Centroid algorithm was used for peak detection.

Figure 1B:
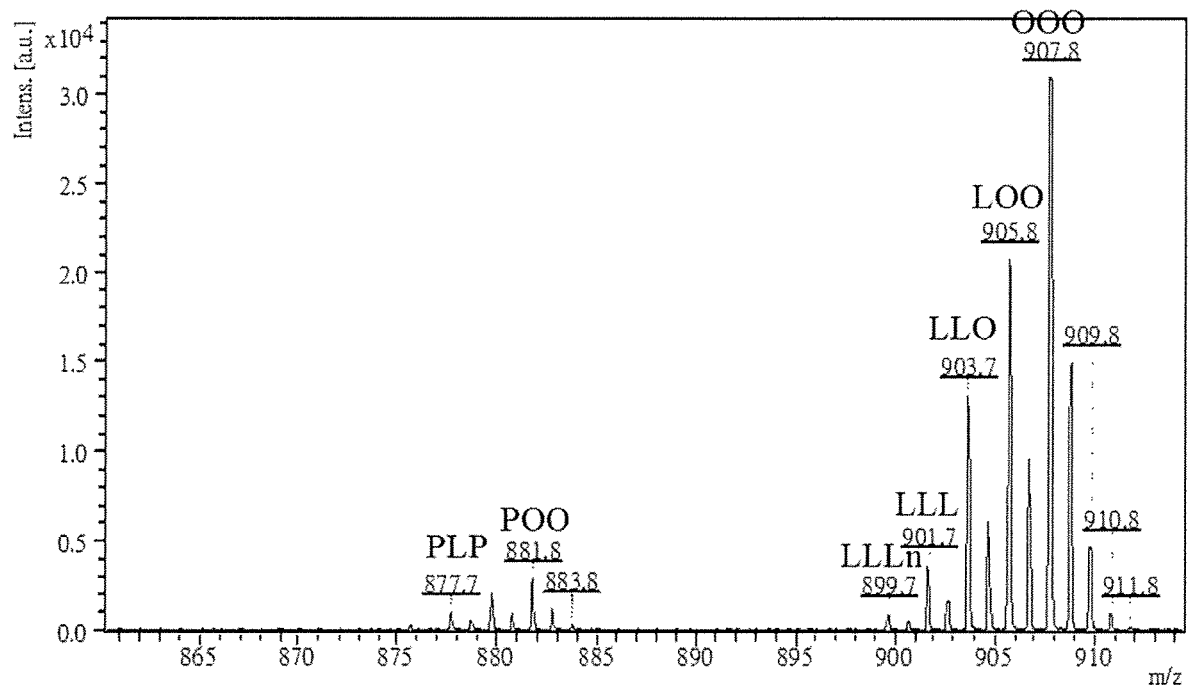
FIG. 1b is an enlarged view of a TAG region of FIG. 1A.
Figure 1C:
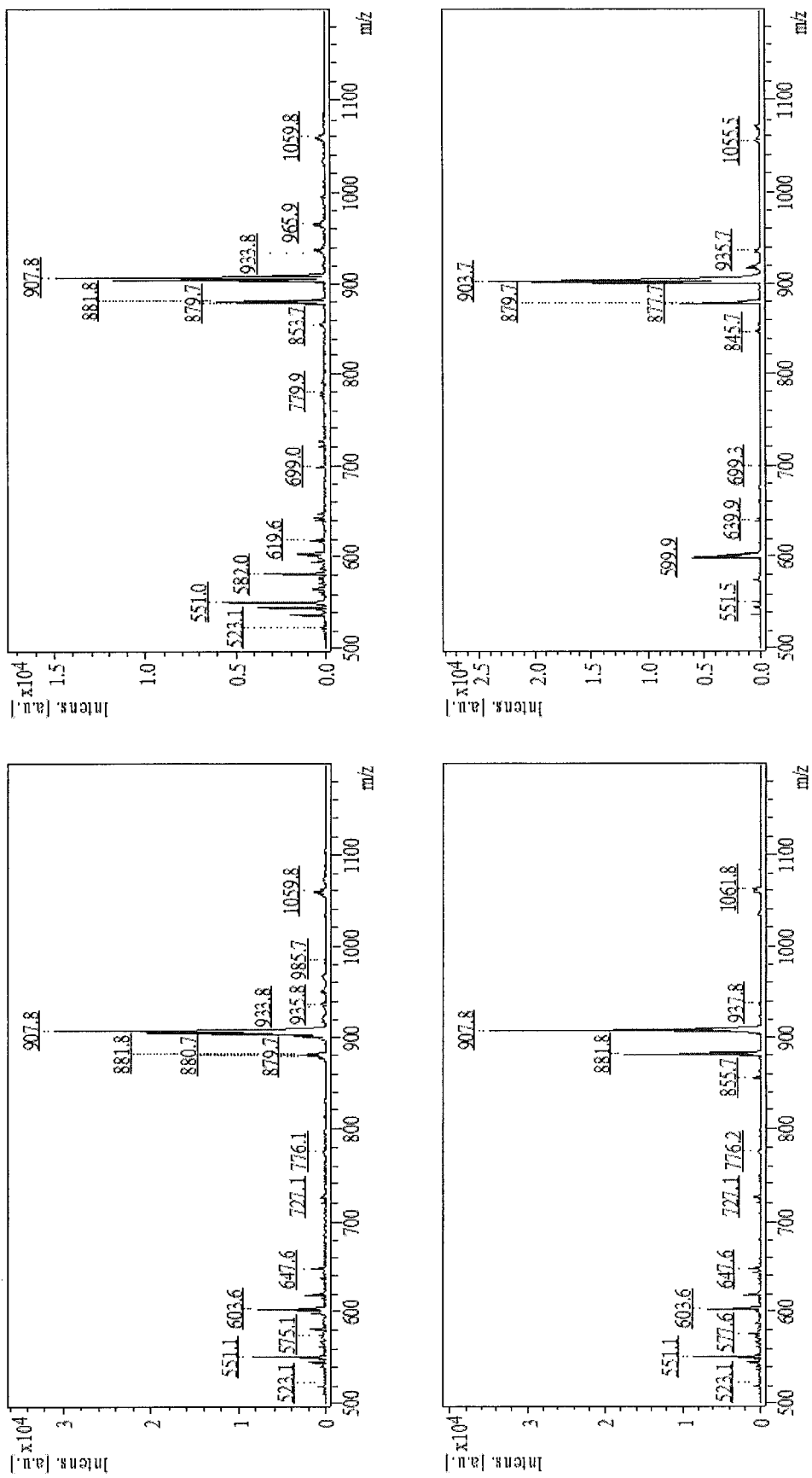
FIG. 1c shows the characteristic peaks of canola, peanut, olive and sunflower edible oils, focussing on the TAG region of these oils.

Referring to the FIGS. 1A-1C there are shown typical spectra resulting from MALDI-MS analysis of selected edible oil samples.

Referring now to FIG. 1A, the results of the full spectra resulting from MALDI-MS spectrum of a canola oil sample from 500-1200 m/z is shown. There can be seem a dominant triacylglycerol peak at 907.8 Da, together with a smaller peak at 881.8 Da. There are also a number of peaks in the fragment region clustered around 603.6 Da. The peaks behind 920 Da are typical of oxidation/thermal products.

Peaks clustered around 935.8 Da can be oxidised TAGs and peak at 1059.8 Da seem correlated with TAGs-fragment cluster ion.

In FIG. 1b, which is an enlarged portion of the region of FIG. 1a from 850-920 m/z, the same two TAG peaks can be seen, with the letters represent various fatty acids, including P (Palmitic Acid), O (Oleic Acid), L (Linoleic Acid) and Ln (Linolenic acid).

Finally, FIG. 1c depicts peaks of MALDI MS spectra for a number of other edible oil samples of different types including (i) canola (ii) peanut (iii) olive (iv) sunflower with their characteristic TAG peaks (and to a lesser extent their DAGs— like peaks).

FIG. 2 depicts TAG peaks of various samples of recycled oils, which were obtained from National Analytical Centre, Guangzhou and which the TAGs patterns appear quite different from pure edible oils of the database.

FIG. 3a-3d depict typical MADLI-MS spectra which have been obtained by analysis of various mixtures of olive and canola oil. Particular emphasis is given to the changes in the characteristic peaks as the relative proportions of the components of the mixture are changed. It can be seen that there is a characteristic TAG peak at 908 Da, with secondary peaks at 882 Da being distinctive indicators for the present of canola oil in FIG. 3a. As shown at FIG. 3a-3e, when the composition of olive oil increases, the intensity of peak at 882 Da increases. The changes in the spectra allowed differentiation of various mixtures of olive and canola oil.

Figure 4A:
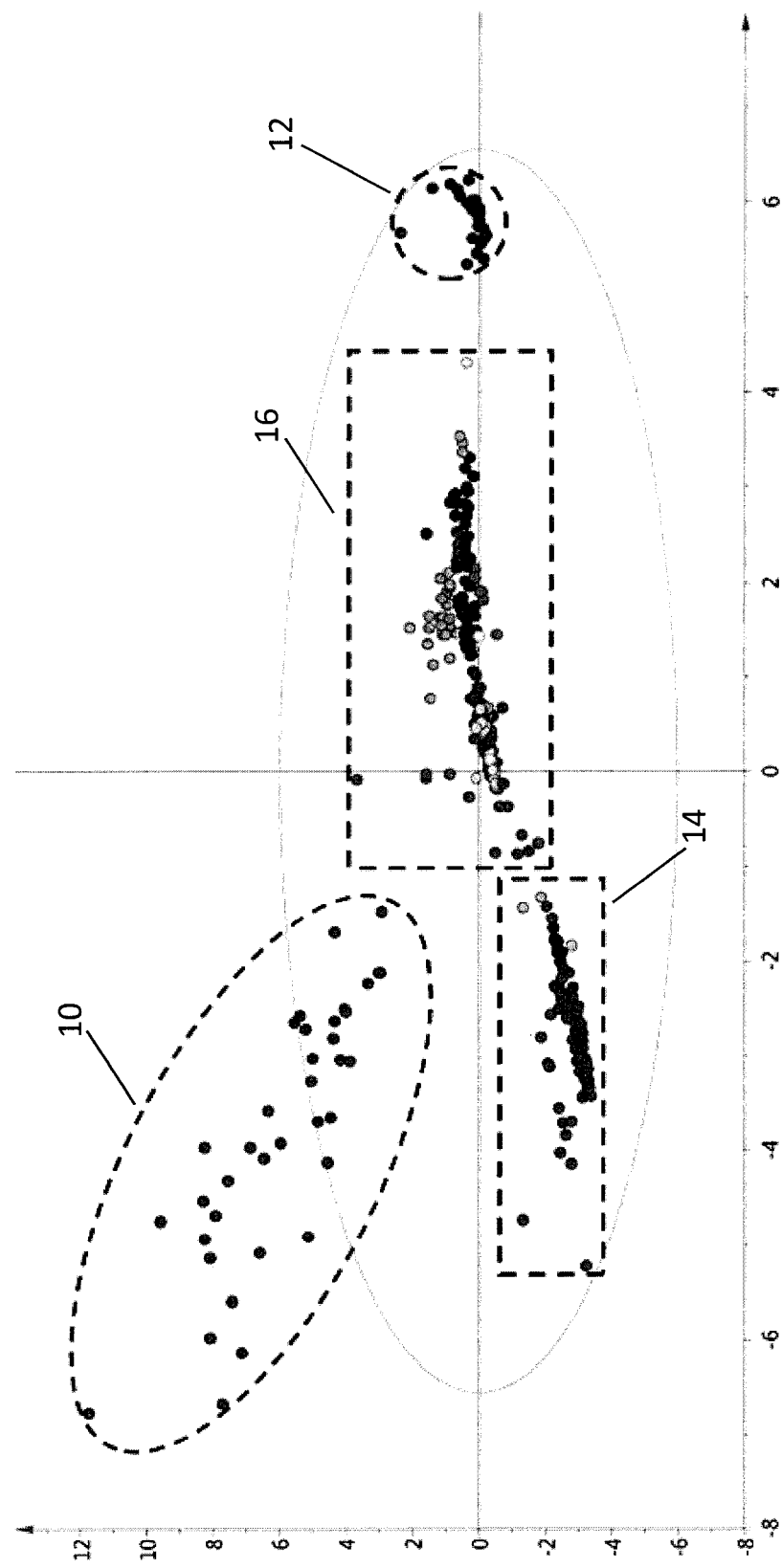
FIG. 4a depicts an exemplary PCA plot of different types of oil in which the oils can be divided into 4 groups (the same results obtained by hierarchical clustering).

Referring now to FIG. 4a, there is shown the output from the prior art approach to sample identification using PCA, once the peaks such as those of FIGS. 1, 2 and 3 have been obtained for a sample.

PCA converts observations of possibly correlated variables into a set of values of linearly uncorrelated variables using an orthogonal linear transform. This technique allows for visualising and processing of high dimensional datasets but at the same time retaining as much of the variance of the dataset as possible.

In conducting the principal component analysis of the sample, a score plot is generated from first and second principal TAG components of the sample.

Results of using PCA on TAG components showed that samples from the same species were clustered individually and different vegetable oil species could be clearly differentiated from each other. (see FIG. 1 below and Ng, T. T.; So, P. K.; Zheng, B.; Yao, Z. P., *Rapid screening of mixed edible oils and gutter oils by matrix-assisted laser desorption/ionization mass spectrometry. Anal. Chim. Acta* 2015, 884, 70-76.)

In FIG. 4a, the results of MALDI-MS on the samples can be divided into essentially four groups, as indicated by the outlines.

Group 1 (10) is likely to be Peanut oil, Group 2 (12) flaxseed, Group 3 (14) vegetable oils with TAGs patterns similar to olive oil and Group 4 (16) other vegetable oils.

Figure 4B:
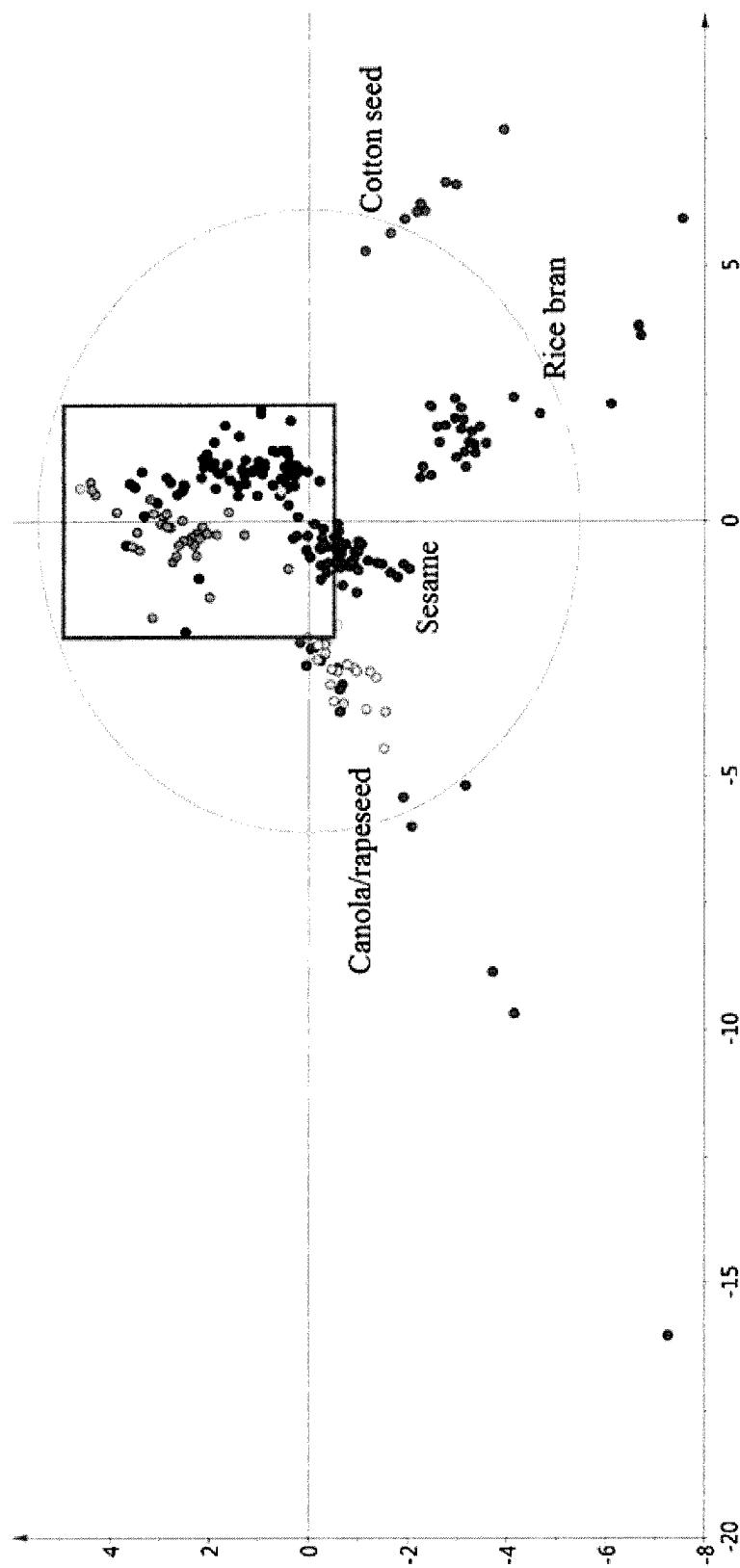
FIG. 4b depicts an exemplary subsequent PCA analysis of group 2 of the plot of FIG. 4a in which a further PCA is conducted to further identify different types of oil.

Referring to FIG. 4b, there can be seen the results of a further PCA analysis in which sub group 2 is further analysed. Samples of canola/rapeseed oil, sesame oil, rice bran oil and cotton-seed oil (spots located at the lower half) are likely to be differentiated from the other oils (spots located at the upper half) in sub group 2. The other oils in sub group 2 will need further PCA analysis to be differentiated completely.

However, as noted in the background to the present invention, PCA analysis suffers from a number of deficiencies which mean that it is not scalable, and must be performed by skilled operators.

Accordingly, the present disclosure provides a method and system which addresses these deficiencies, and which enables a robust, scalable technique for analysis, verification and identification of edible oils.

Figure 5A:
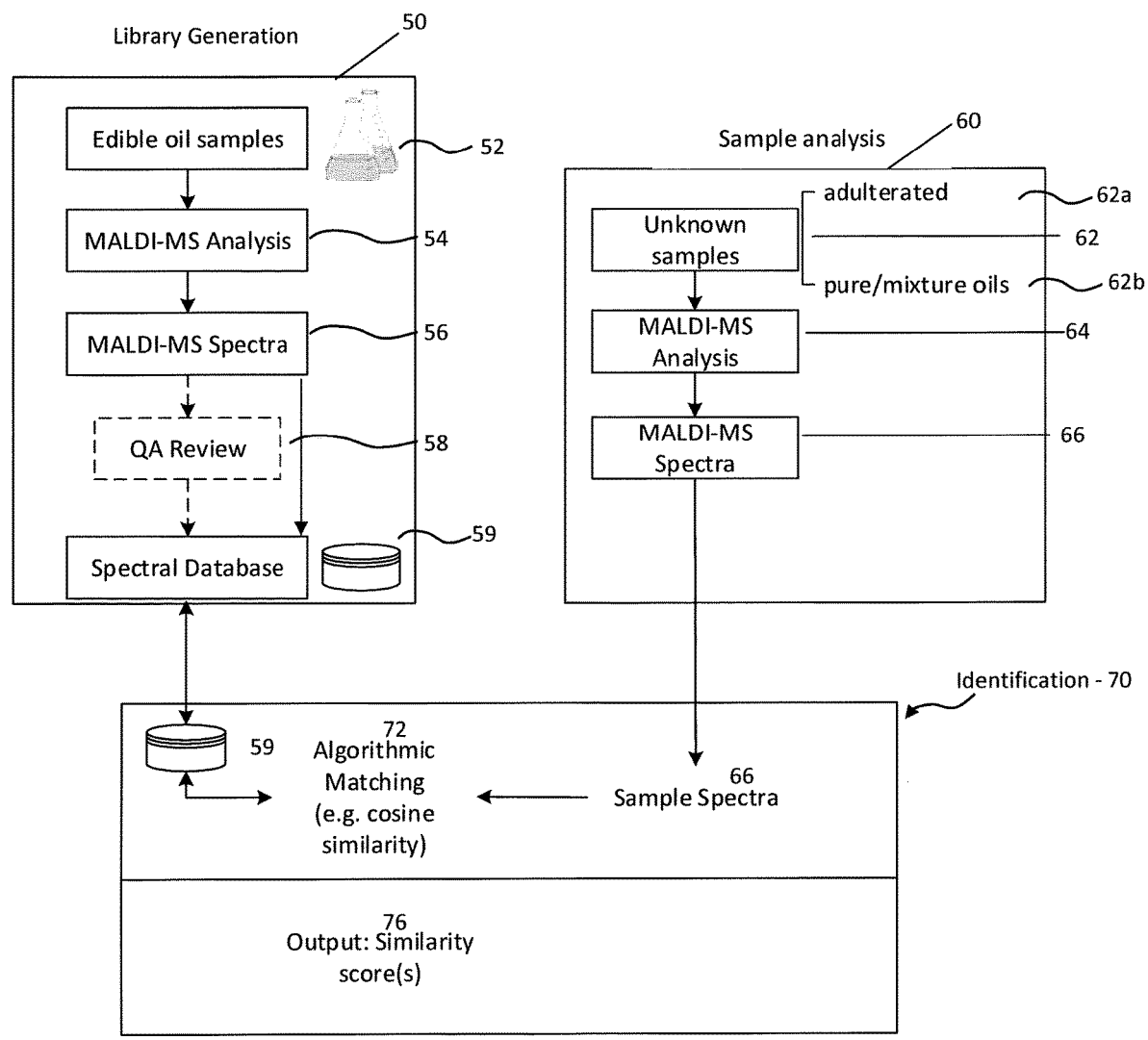
FIG. 5a depicts an exemplary flow diagram an embodiment of the system of the present disclosure.

Referring to FIG. 5a, there can be seen the three main groups of steps in the method and system of the present disclosure.

Referring to component 50, there is disclosed a series of steps associated with producing a library of MALDI-MS spectral data. A plurality of edible oil samples having a known type and origin are selected for assessment at step 52. In the library produced, we have selected up to six hundred samples from various suppliers, including from Mainland China, Taiwan, Hong Kong, and Sigma-Aldrich in the USA. Multiple instances of one type oil from different sources have been selected in many cases to provide a complete database.

These samples are subjected to a MALDI-MS analysis as disclosed at the protocols of the present disclosure in step 54.

The MALDI-MS spectra obtained from the analysis at step 56 are passed through an optional quality assurance review at step 58 involving review by a trained operator. During this review, the operator reviews the calibration and resolution of the spectrum in order to ensure that the best reference spectra are included in the library. A high level of oxidised products and/or poor calibration will cause the data to be rejected by the human reviewer. It would be appreciated that although this step is optional, particularly in the generation of a library of spectral data, review of the spectral data to ensure that readily apparent errors or tainted samples are rejected which in turn increases the integrity of the library of spectral data obtained.

Following the quality assurance review, the MALDI-MS spectra are stored in the spectral database at step 59, thereby forming a library of spectral data of edible oil samples. Optionally, in order to increase the accuracy of the presumptive identification made using the samples in the library, a plurality of different samples for a known oil type may be obtained from a number of different manufacturers, it is anticipated that notwithstanding the origin of the oil being from a number of different manufacturers that a fairly similar spectra will be observed.

A further part of the system of the present disclosure includes the sample analysis system referred to at box 60 of FIG. 5a. It would be appreciated that the sample analysis allows for the detection of adulterated oils (62a) oils (cheaper oils mixed with expensive oils and mislabelled as pure, often more expensive oils) and "gutter"—oils which have been used already for cooking and have been recycled—as well as the identification of pure edible oils from an unknown sample or mixtures of edible oils from an unknown sample (62b).

The unknown samples are subjected to MALDI-MS analysis at step 64 in accordance with the earlier described protocol of the present disclosure to produce the sample MALDI-MS spectra at step 66.

Referring now to the identification component of the present disclosure 70, the series of steps in an exemplary identification system is described in overview.

The sample spectra 66 are matched at the algorithmic matching step 72 by a processor of a computer. The algorithmic matching may be a form of comparison such as a cosine similarity test or similar by which the sample data 66 is compared against the spectral database 59 which has been obtained for a plurality of edible oil samples in the library generation component 50. This process is disclosed in more detail with reference to FIG. 5b.

The outcome of the algorithmic matching between the sample spectra 66 and the spectral database 59 is one or more similarity scores according to the edible oil samples present in the library.

As is appreciated by a person skilled in the art, the higher the similarity score produced by whatever algorithm is used for matching the spectra of the sample with the corresponding spectra in the edible oil library, the higher the chance of presumptive identification of the unknown edible oil sample.

It would be appreciated that this process is similar, notwithstanding whether the unknown edible oil sample is an adulterated edible oil sample, a pure edible oil sample or a mixture of edible oils—the matching with the library via the algorithm and resulting presumptive identification will be generally the same.

Figure 5B:
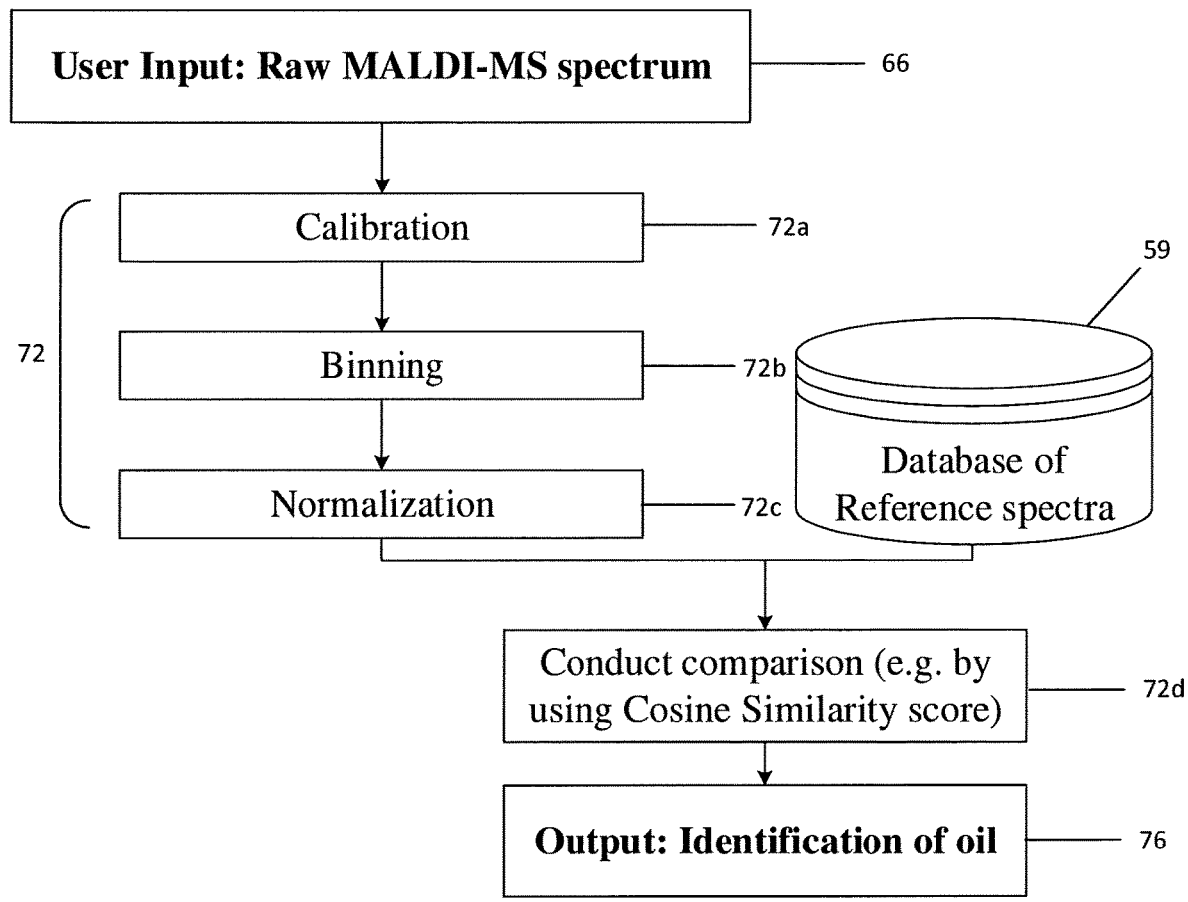
FIG. 5b depicts the core of the flow diagram of FIG. 5a and how the workflow proceeds.

Referring now to FIG. 5b, the process for the processing of the spectra of an unknown sample is disclosed in more detail. At 66 the user supplies the raw MALDI-MS spectra for analysis. It would be appreciated that this could be supplied as a data file to a central processing facility which is geographically remote from the place at which the MALDI-MS spectra was performed. Alternatively, the spectra and the processing could be conducted at the same facility, without detracting from the present disclosure.

Once the raw MALDI-MS spectra have been obtained from user input, this spectra is calibrated at step 72a. Calibration is typically conducted using prominent TAG peaks and the DHB matrix peaks as a reference. This calibration process ensures that the samples are standardized, for ease of analysis and reproducibility of analysis against the library of standardized edible oil spectra peaks.

Alternative matrixes could also be used such as CHCA (α-Cyano-4-hydroxycinnamic acid) and SA (sinapinic acid). Based upon whichever matrix was used appropriate calibration with the characteristic peaks could also be performed. However, it was noted that the background noise were higher if CHCA were used, and the signal intensity were very poor if sinapinic acid was used as the matrix.

To assist in obtaining reproducible results, as a matter of best laboratory practice the mass spectrometer should also be calibrated with a PEG solution mixture (PEG600/PEG1000/PEG2000/NaI=1/2/2/5 (v/v)) before conducting analysis.

Following calibration, a binning process is conducted on the data at step 72b. As is known to persons skilled in the art, data binning or bucketing is a data pre-processing technique which quantizes the data. Basically, in data binning, the original data series values which fall in a given small window or bin are replaced by a value which is a representative of that interval, often the centre value.

As is known in the art, data binning reduces the amount of data (necessarily losing information) but facilitating analysis. In the MALDI-MS spectra analysis, the typical size of bin was 0.5 m/z, although other sizes could be used. It would be appreciated by a person skilled in the art that an increased bin size will decrease the resolution of the data obtained. The size of bin affects the accuracy and quality of the matching, and the optimal size of the bin represents a balance between too much detail and too low resolution.

In an exemplary embodiment of the present invention the data binning process used was dividing the entire spectra into intervals of 0.5 m/z, averaging the intensity of all readings within each bin, and setting the m/z reading as the m/z value at the middle of the interval.

Following the data binning process at step 72b, the data was normalized by dividing the intensity of each bin with the maximum intensity of all bins, multiplied with 10000 and rounded to the nearest integer.

Alternatively, in an alternative process of normalization, the sample data could be normalised by dividing the intensity of each bin with the total intensity of all bins, and then multiplying the result by 10000 and rounding.

Following the normalization process, the unknown sample data which has been calibrated, binned, and normalized, is compared against a database of reference spectra of edible oils (where the information in that database is for edible oils which have been similarly calibrated, binned and normalized) in step 74. This comparison may be conducted using a cosine similarity approach.

As is known in the art, cosine similarity matching is a measure of similarity in which the samples of unknown sample spectra is represented as a vector; and for which the dot product of that sample with a plurality of vectors representing the sample data in the library is obtained.

Cosine similarity calculates the cosine of the angle between two vectors.

Where vectors are in generally the same direction, the cosine of the angle between the two vectors is near to 100% or 1. However, where the vectors (abstractions of the spectral data) are orientated in different directions, the cosine of the angle between the two vectors which is obtained by the dot product solution is near zero; that is 0%. Furthermore, where the vectors are in completely different directions, the cosine similarity obtained is −1.

Accordingly, the cosine similarity is a useful algorithm to obtain a numerical score which represents the degree of similarity between two spectra.

Optionally, other data processing technique such as characteristic peak matching methods (mainly for detecting the presence or absence of oxidation products or cyclopeptides), partial least squares discriminant analysis (PLS-DA), or decision-tree based techniques (e.g. random forest) could also be used to compare the calibrated, binned and normalized MALDI-MS sample data with the similarly calibrated, binned and normalized data of the reference spectra.

The outcome of the process at step 76 is the identification of the oil.

Advantageously, as is depicted in successive Figures, it may be provided in the form of a ranked series of scores of cosine similarity for a plurality of samples of the library, or alternatively may be simply selected as the highest score identification.

Figure 6A:
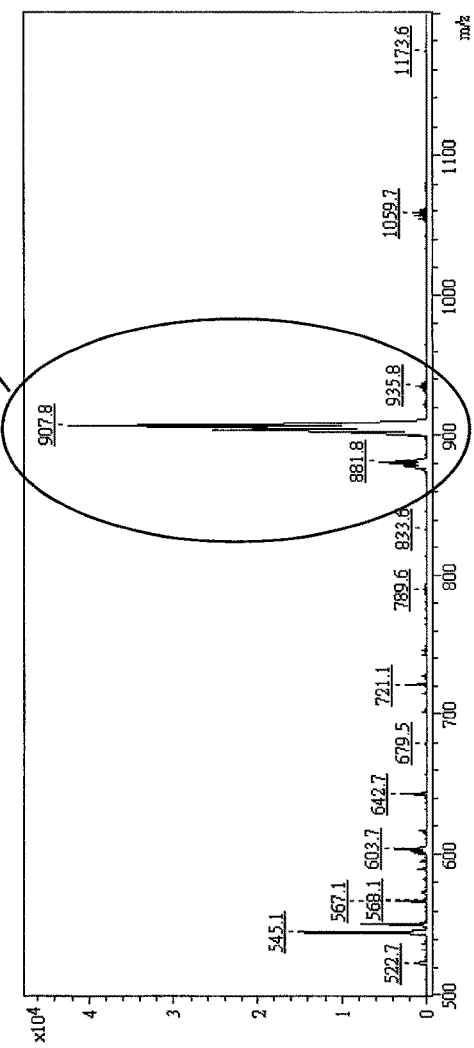
FIG. 6a shows the exemplary data of characteristic spectra stored for a known sample of a library database, depicted graphically to the user.
Figure 6B:
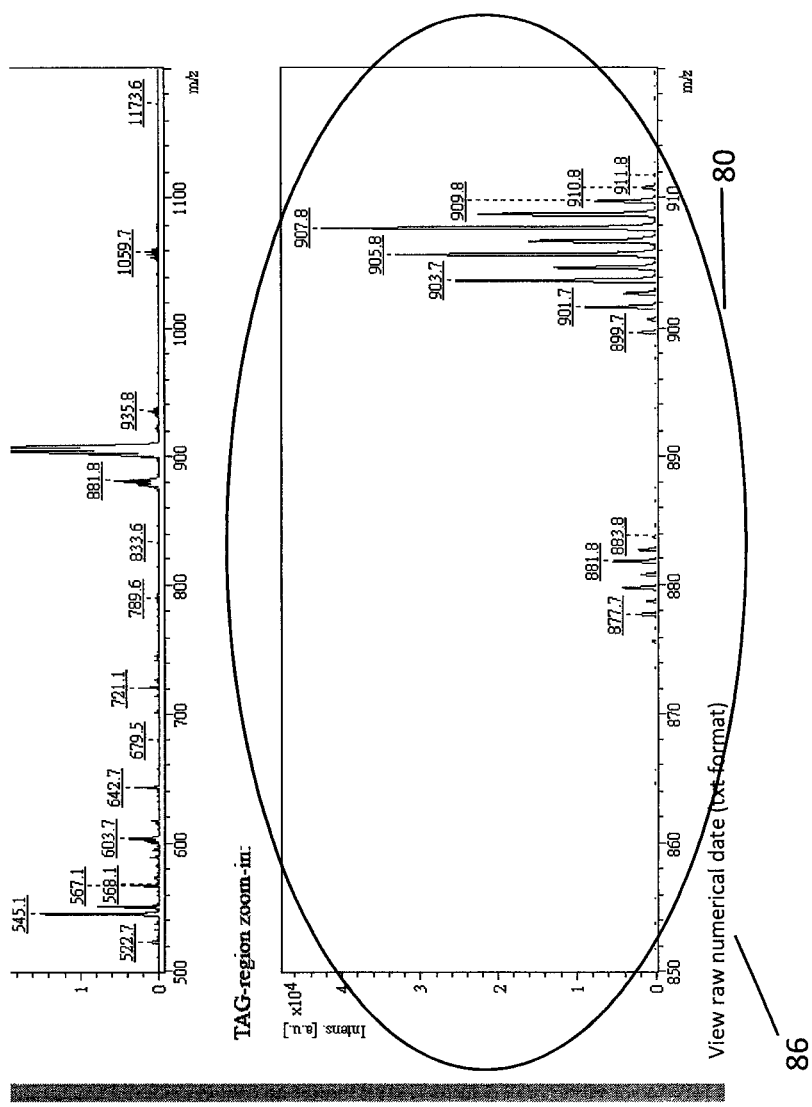

Referring now to FIG. 6a, there can be seen an exemplary reference spectra for an edible oil sample S88 (canola). The prominent TAG peak region 80 is circled in FIG. 6a for ease of reference and further extracted in FIG. 6b in an enlarged view.

On the left hand side of the sample, it can be seen that there are a plurality of samples of canola oil 82 in which the details of the manufacturer and collection source have been recorded at 84.

There is also optionally the ability to view the raw numerical data in text format by selection of the link 86.

Most edible oils have one group of TAG peaks at around 870-885 Da, and another group of TAG peaks at 900-910 Da. Some edible oils such as coconut oil would have their TAG peaks at different region. For each type of oil, the ratio of each TAG is largely determined by the enzymes of the parent species. Therefore, the relative intensities of peaks within the TAG region are specific for each types of oil, and the intensities of the peaks form a distinctive shape for each types of oil. Hence, the location and shape of the TAG regions could be used as a fingerprint to identify the oil type of an unknown.

Accordingly, the present disclosure provides the ability for users to view, for example, by browsing the reference spectra of multiple different types of edible oils, and in many cases, for multiple samples of a particular edible oil.

This sample reference data may be stored as a series of raw numerical data, but represented for ease of human interpretation in the graphical format depicted.

Referring now to FIG. 7a, the output from the authentication process of an unknown oil sample can be seen. Advantageously, the file may be included at the portion of the screen indicated by FIG. 88 and the output indicated by the correlation score shown in the region below at 90. In this example, the unknown oil spec in text format has been presumptively identified as a palm oil with a relatively strong correlation score of 0.9959.

Referring now to FIG. 7b, it can be seen that there are two samples which have been provided at the outputs presented, at 92 and 94 respectively.

For the sample identified at 92 as butter, the correlation score is relatively lower (0.9410) meaning that there is not as much confidence in the presumptive identification.

Similarly at 94, the edible oil identified is pumpkin seed oil, however the correlation score is also relatively low.

(Note: The 'low score' may depend on the usage. If the user just wants to identify an unknown with no other information, the user may be satisfied with a score of 0.97, as it would be the closest match.

However, if the user wants to know if an oil with known type has been adulterated or heated for some time, the threshold for correct matching needs to be higher, as a lower score would mean that the TAGs in the oil has been changed somehow.

Generally speaking, based upon the experimental data obtained to date a threshold score of 0.97 seems to be a reasonable level for most purposes.)

These results may be compared to the high correlation score shown in FIG. 7a for palm oil.

Accordingly, the user reviewing these results in view of the weak correlation scores would be less confident of the presumptive identifications of the latter samples.

Figure 8A:
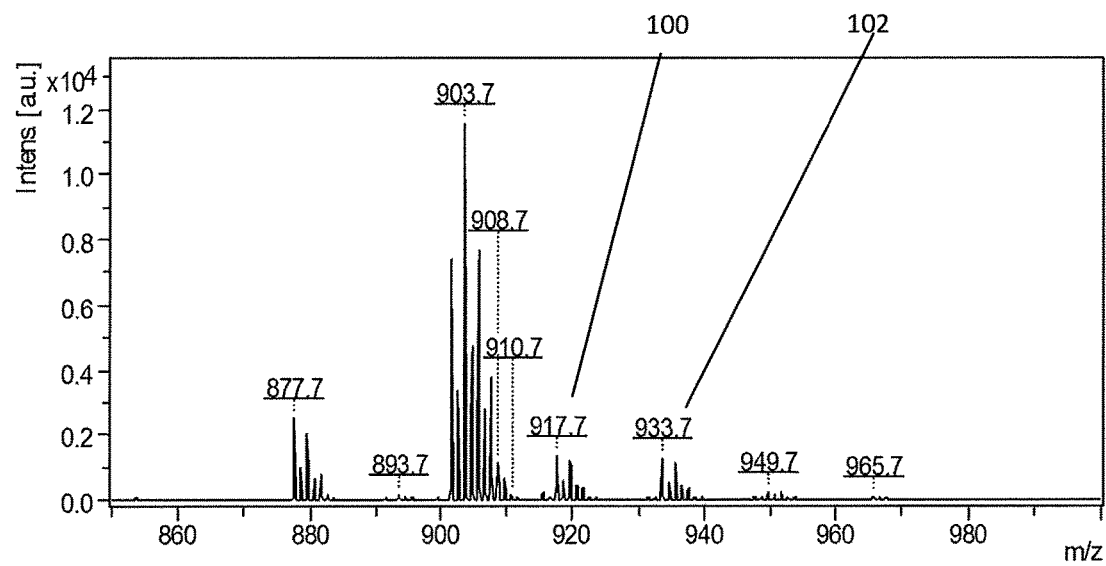
FIG. 8a is an exemplary sample of a bad TAG spectrum of sunflower oil which would not be stored in the database.

Referring now to FIG. 8a, there can be seen exemplary spectra of poor quality. As represented by peaks at 917.7 and 933.7 (100 and 102 respectively), there is a high level of oxidation products present in the sample. Accordingly, with human quality assurance step of FIG. 5A (58), this sample would not be included in establishing the spectral database Alternatively, if these samples were obtained from an unknown sample the system would generate a poor correlation score against the oil spectra in the database, and the user would know that the oil has been somehow modified (adulterated, heated, stored for too long, etc.).

Figure 8B:
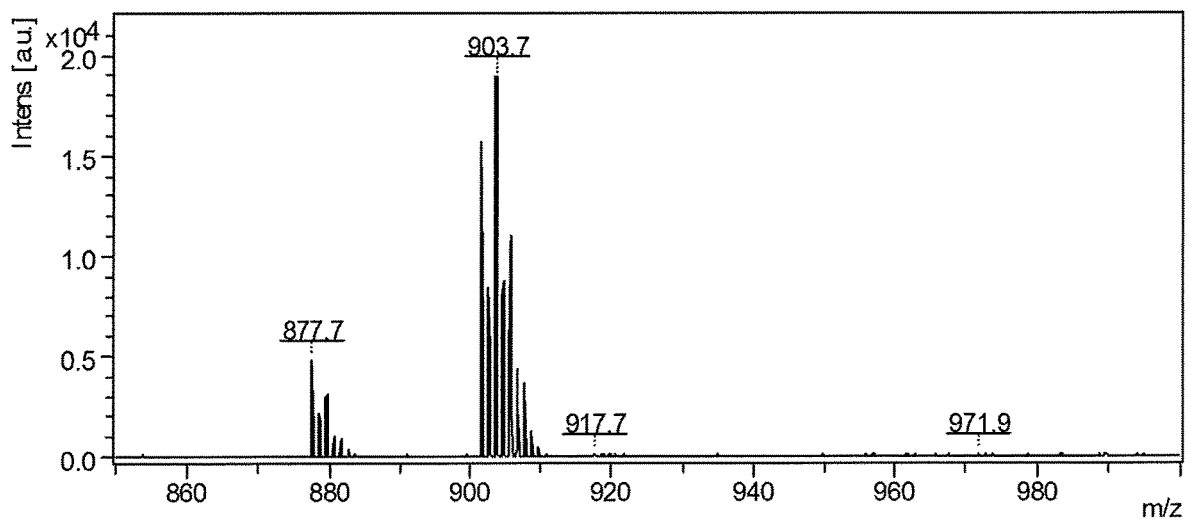
FIG. 8b is an exemplary sample of a good TAG spectrum of sunflower oil which would be stored in the database as a reference sample.

Referring now to FIG. 8b, there can be seen a much better spectrum of a normal sunflower oil sample in which the oxidation products 100, 102 are clearly not present.

Figure 9A:
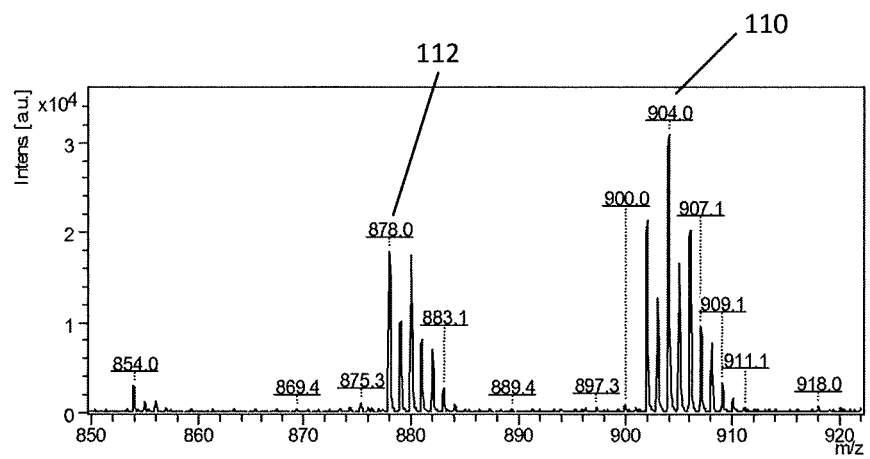
FIG. 9a is an exemplary sample of a mass spectrum analysis of a corn oil in which calibration has not been conducted properly.

Similarly, referring now to FIG. 9a, there is depicted a poorly calibrated spectrum for corn oil, in which the typical TAG peaks associated with corn oil have been shifted 0.3 Da to the right.

Figure 9B:
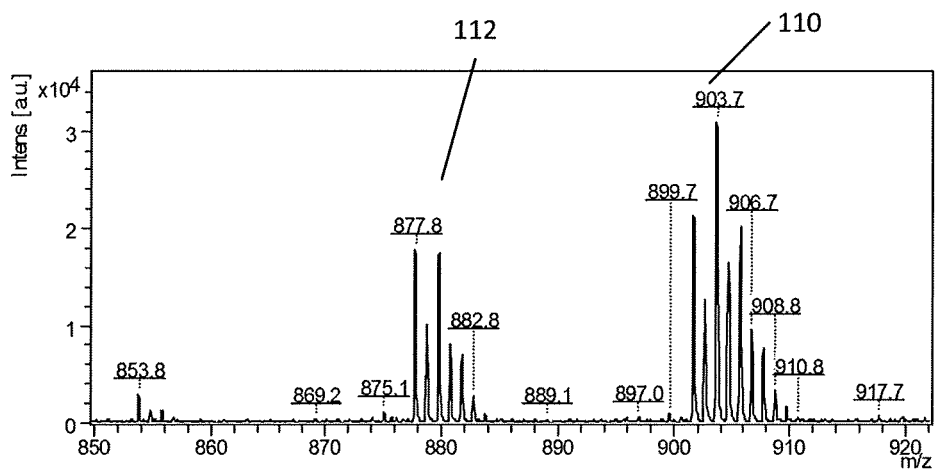
FIG. 9b shows the same sample of a corn oil after calibration has been conducted properly
Figure 9C:
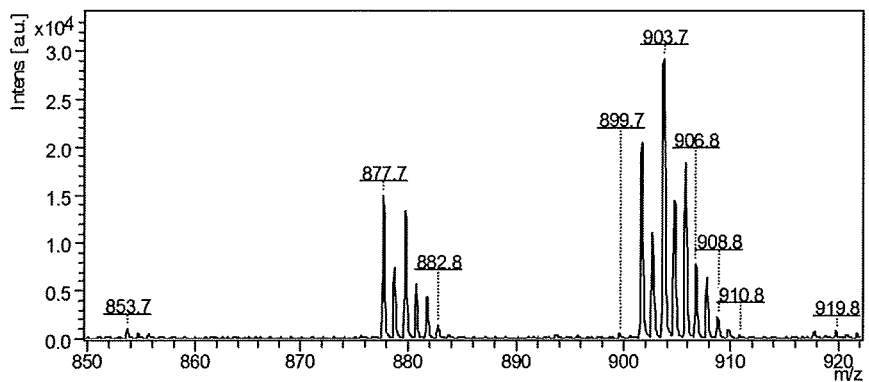
FIG. 9c shows the reference sample of TAG spectrum for corn oil for reference.

This is apparent when the spectrum or the poorly calibrated spectrum of FIG. 9a is compared to the reference spectrum of FIG. 9b, the TAG peaks are 110 and 112 are clearly displaced and accordingly the spectra of FIG. 9a after calibration is adjusted by 0.3 Da to provide the properly calibrated spectra as depicted in FIG. 9c.

Figure 9D:
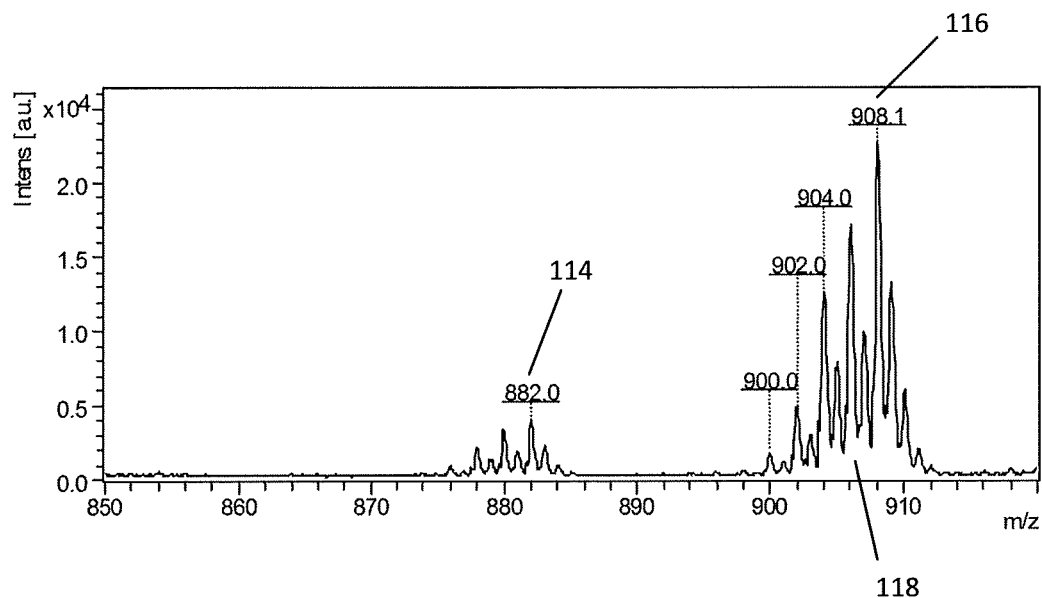
FIG. 9d shows another sample in which the TAG spectrum of camellia oil is poorly calibrated and has poor resolution.

Another example of poor calibration and resolution can be seen in FIG. 9d in which the TAG pattern of camellia oil is depicted. It can be seen looking at the characteristic peaks 114 and 116 for this camellia oil sample that again the sample has been poorly calibrated, and suffers from poor resolution in the region 118 between 900 and 910. The peaks obtained should be sharp and the baseline should be low. Characteristic peaks in FIG. 9d seen too broad and the baseline is raised.

Figure 9E:
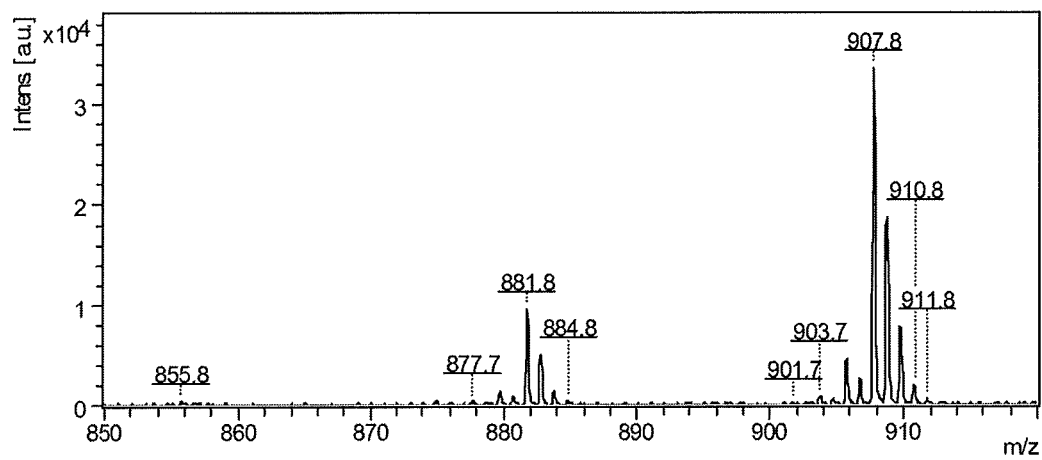
FIG. 9e shows the sample of FIG. 9d in which the resolution and calibration has been rectified.

Accordingly, following review and quality assurance being performed by an operator, as depicted in FIG. 9e, the re-analysis of the TAG camellia oil sample gives a much better more robust spectra, in which the calibration and resolution problems have been addressed.

Referring to FIG. 10a, there is a further example of the necessity for quality assurance to be conducted on the samples which form the reference library.

Figure 10B:
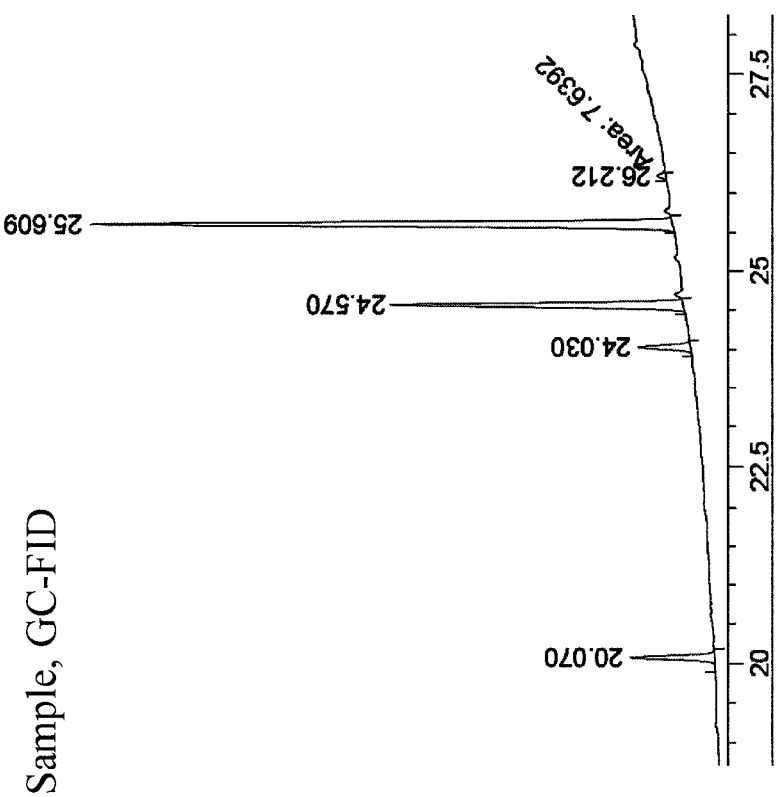
FIG. 10b shows the GC-FID analysis of the sample which supports the conclusion this sample has been mislabelled.

It can be seen that the problematic sample of spectra in 10a (i) has an entirely different peak pattern of the flaxseed oil samples depicted in 10a (ii) and 10a (iii). Following the identification of the mis-match, between the claimed reference sample of flaxseed oil and the other reference samples in the reference library, the problematic sample could be subjected to a GC-FID analysis. As depicted in FIG. 10b, the outcome of such analysis reveals that the sample has indeed been mislabelled and the sample would no longer be included in the reference database as being flaxseed oil.

Accordingly, the integrity of the reference library for identification of the edible oil samples can be increased.

The present invention provides an advantageous, potentially scalable method of identifying edible oils. This enables the rapid detection of mislabelled edible oils, the identification of adulterated oils and gutter oils, as well as the ability to authenticate labelled oil spectra.

It is also possible for the major and minor elements of the mixed oil to be identified, through comparison with reference samples such as those depicted in FIGS. 3a to 3e in the reference library.

In this usage, the user can check the relative proportions claimed on the label of the edible oil with the actual detected compositions.

Another advantage of the present invention is that the MALDI-MS analysis can be conducted at an analytical laboratory and the reference library may necessarily be located at a location which is geographically remote from that analytical laboratory. The presumptive identification can then take place over the internet, with the data simply uploaded onto an appropriate website.

The analysis and presumptive identification of the edible oils can be carried out by as a routine laboratory procedure, without the need for ongoing training or exhaustive statistical analysis.

The algorithm used for matching the spectra provides a reliable, scalable and efficient way of presumptively identifying a wide variety of edible oils against a reference library.

The inclusion of the automated data matching process removes the need for human matching of the reference spectra.

Unlike previous PCA approach, the algorithm does not need to be modified if a new type of oil is added to the database.

The results can also be displayed to the user automatically, which is not possible with the previous approaches.

The above embodiments are described by way of example only. Many variations are possible without departing from the scope of the invention as defined in the appended claims.

For clarity of explanation, in some instances the present technology may be presented as including individual functional blocks including functional blocks comprising devices, device components, steps or routines in a method embodied in software, or combinations of hardware and software.

Methods according to the above-described examples can be implemented using computer-executable processes that are stored or otherwise available from computer readable media. Such processes can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, universal serial bus (USB) devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

Although a variety of examples and other information was used to explain aspects within the scope of the appended claims, no limitation of the claims should be implied based on particular features or arrangements in such examples, as one of ordinary skill would be able to use these examples to derive a wide variety of implementations.

Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

The invention claimed is:

1. An edible oil sample identification system comprising:
a library comprising a plurality of calibrated matrix-assisted laser desorption/ionisation mass spectrometry (MALDI-MS) spectral data for a plurality of edible oil samples; and
a processor configured to:
receive MALDI-MS data for at least one or more edible oil samples,
calibrate the MALDI-MS data derived from the one or more samples, and
compare the calibrated MALDI-MS data with the library to determine a predicted composition of the one or more edible oil samples; wherein such comparison does not include principal component analysis (PCA) analysis, and
wherein calibration of the MALDI-MS data for the one or more samples uses reference peaks selected from triacylglycerol (TAG) peak(s) and 2,5-dihydroxybenzoic acid (DHB) matrix peak(s) of the MALDI-MS data of the one or more samples, and calibration of the MALDI-MS spectral data of the library uses reference peaks selected from triacylglycerol (TAG) peak(s) and 2,5-dihydroxybenzoic acid (DHB) matrix peak(s) of the MALDI-MS spectral data of the plurality of edible oil samples in the library.

2. The edible oil sample identification system according to claim 1 wherein the processor is configured to compare the calibrated spectral data derived from the one or more samples with the library using a cosine similarity test, and to output the determined cosine similarity score for a plurality of samples of the library.

3. The edible oil sample identification system according to claim 2 wherein the processor is configured to conduct the cosine similarity test on one or more regions of the sample spectral data selected from the group comprising high mass, low mass and TAG regions and one or more corresponding regions of the data in the library.

4. The edible oil sample identification system according to claim 1 wherein following calibration and before comparison against the calibrated library data, the processor is configured to quantise the sample data by data binning.

* * * * *